United States Patent [19]

Brown et al.

[11] Patent Number: 5,417,835
[45] Date of Patent: May 23, 1995

[54] SOLID STATE ION SENSOR WITH POLYIMIDE MEMBRANE

[75] Inventors: Richard B. Brown; Geun-Sig Cha, both of Ann Arbor, Mich.

[73] Assignee: The Board of Regents of The University of Michigan, Ann Arbor, Mich.

[21] Appl. No.: 137,373

[22] Filed: Oct. 14, 1993

Related U.S. Application Data

[63] Continuation of Ser. No. 746,134, Aug. 13, 1991, abandoned, and a continuation of Ser. No. 370,897, Jun. 23, 1989, abandoned.

[51] Int. Cl.$^6$ ............................................. G01N 27/26
[52] U.S. Cl. ................................. 204/403; 204/418; 257/253; 257/414; 435/817
[58] Field of Search ................. 204/418, 416, 403; 257/253, 414; 435/288, 291, 817

[56] References Cited

U.S. PATENT DOCUMENTS

| | | | |
|---|---|---|---|
| 4,020,830 | 5/1977 | Johnson et al. | 128/635 |
| 4,486,292 | 12/1984 | Blackburn | 204/416 |
| 4,613,422 | 9/1986 | Lauks | 204/419 |
| 4,871,442 | 10/1989 | Yamaguchi et al. | 204/418 |

Primary Examiner—Kathryn Gorgos
Assistant Examiner—William T. Leader
Attorney, Agent, or Firm—Rohm & Monsanto

[57] ABSTRACT

A polyimide matrix is employed to form a substance-sensitive membrane which is particularly suited for installation on a solid state sensor. Polyimide, dissolved in a solvent, such as N,N-dimethylformamide, or N-methyl-2-pyrrolidone (polyimide encapsulant), is combined with an ionophore, plasticizer, and a lipophilic additive. The ionophore may be a calcium ionophore, an ammonium ionophore, or any other ionophore. The membrane may also incorporate, or may be covered by, a bioactive agent, such as an enzyme, an immunochemical, bacteria, antibody, virus, or antigen. The plasticizer is one or both of dimethyl phthalate and diethylene glycol dibenzoate. The lipophilic additive may be potassium tetrakis(p-chlorophenyl)borate. The resulting substance-sensitive membrane has electrochemical properties which compare favorably to those of conventional PVC membranes, and exhibit significantly greater adhesion to glasses and semiconductor substrate materials. The improved adhesion may prolong the life of the sensors and prevent the formation of electrolyte shunts which have been known to render solid state sensors inoperative.

13 Claims, 4 Drawing Sheets

SOLID STATE ION SENSOR WITH POLYIMIDE MEMBRANE

This application is a continuation of U.S. application Ser. No. 07/746,134 filed on Aug. 13, 1991, now abandoned as a continuation of U.S. application Ser. No. 07/370,897 filed on Jun. 23, 1989, now abandoned.

BACKGROUND OF THE INVENTION

This invention relates generally to devices and systems for measuring concentrations of ions, chemicals, biological materials, and reaction products, and more particularly, to a solid state device which employs a polyimide-based matrix as the substance-sensitive membrane and wherein the substance-sensitive membrane is installed using conventional integrated circuit fabrication techniques.

Polyimide has been used in the fabrication of integrated circuitry, particularly as a surface protection layer and as a dieleatric material between metal interconnect layers. Polyimide films are also known to be flexible, strong, and insoluble. In addition, the adherence of polyimide to materials which ordinarily are used in the fabrication of such circuit systems to form integrated circuit surfaces is well known. Examples of the materials to which polyimide adheres well include, $SiO_2$ and $Si_3N_4$. Surfaces formed of these materials are commonly employed in the structure of solid state sensors.

It is additionally known that polyimide exhibits significant mechanical strength, and has been used to provide enhanced mechanical support to certain structures. A polyimide layer will form a strong and mechanically rigid coupling between silicon-based materials and structural layers which are relatively weak, such as those formed of boron nitride.

Polyimide is easily incorporated into the manufacturing processes of integrated circuits. Although it is not photosensitive, it is easily patterned with conventional photoresist, employing a photomask. Moreover, polyimide is easily etched, and mask layers are easily stripped therefrom.

Silicon and polyimide have been combined in the art to produce a precursor which is useful in the production of a coating which is characterized with a strong adhesion to silicon wafer, glass, etc. In addition, polyimide precursor improves layer strength and hardness. Such precursors have been used as coatings for electronic materials, surface-protecting films, insulating films, and liquid crystal aligning agents. Polyimide precursor materials are also known to exhibit superior adhesion onto silicon wafer, glass, or the like, in addition to superior strength and hardness after baking.

In addition to its employability as a structural element in the fabrication of integrated circuit systems, polyimide has been used to form porous structures in the form of semipermeable membranes. This aspect of polyimide is unrelated to integrated circuit fabrication, and results in the production of asymmetric membranes which have a porosity appropriate for ultrafiltration and reverse osmosis, for example. Such asymmetric membranes are generally prepared by precipitation or phase inversion reaction. The membrane is dissolved in a solvent, spread into a film, and precipitated in a nonsolvent. The resulting membrane is suitable for the desalination of sea water.

In one known system, asymmetric membranes from polyimides are produced by preparing membranes having asymmetric structures from acid amides of the type which can be converted to polyimides according to conventional precipitation or phase inversion reaction. The acid amide membranes are converted subsequently to polyimide membranes by thermal or chemical ring closure reaction. One known reaction scheme commences from a tetracarboxylic acid dianhydride and a diamine to form, by means of an acid amide, a polyimide. The dianhydride, or an equivalent reaction, such as an acid chloride or the like, and the diamine, in an appropriate solvent, are reacted at room temperature whereby a polyamide is obtained in the form of a soluble polymer. The polyamide is then converted to the corresponding polyimide by heating to 300° C. or by chemical reaction. Alternatively, polyimides can be made by reaction of dianhydrides with other nitrogen-bearing polyfunctional compounds such as diisocyanates.

In addition to the desalination of sea water, polyimide membranes have been used in other purification processes, such as the purification of crude glyceride oil compositions, whereby the crude glyceride oil composition with impurities in the form of gum material and wax are diluted with an organic solvent and brought into communication with a semipermeable membrane formed of polyimide, under pressure. Polyimide membranes of this known type are useful in the removal of impurities which include phospholipids, such as lecithin; waxes, such as higher alcohols; organic sulfur compounds; free fatty acids; peptides; hydrocarbons; carbohydrates; lower aldehydes; lower ketones; dye compounds; and some sterols.

Polyimide membranes have found wide acceptance in the field of gas separation. Such gas separation membranes include those in which the molecular structure is such that the molecules in the polymer are unable to pack densely, and therefore have high gas permeability; those formed of aromatic polyimide prepared from polyamide acid membranes; those formed from microporous aromatic polyimide membranes, and which optionally are treated with modifying agents; those formed from a microporous aromatic polyimide support coated with an aromatic polyamide acid or aromatic polyimide; those in which the molecular structure is such that the molecules in the polymer can pack densely; those comprising as essential components thereof a saturated linear polyester or polyamide, and having copolymerized therewith benzophenone tetracarboxylic groups which are cross-linked by irradiation; those formed of aromatic polyether imides; those formed from a microporous aromatic polyimide support coated with a cross-linked silicon resin film; and aromatic polyimide reverse osmosis membranes. Polyimide membranes which are not intended for use as gas separation membranes include those formed from substituted aromatic polyimides and photochemically cross-linked compositions thereof.

In addition to the foregoing, those aromatic polyimides derived from diamines having substituents on all portions ortho to the amine function or from mixtures of aromatic diamines, particularly where some components have substituents on all positions ortho to the amine functions, exhibit high gas permeability. Such membranes are in widespread use in systems where it is necessary to select one gas over other gases in a multicomponent gas mixture. Generally, such selectivity is controlled by selection of the amount of aromatic diamines having substituents on all positions ortho to the amine functions, and/or the amounts of structurally-nonrigid dianhydrides utilized in the polyimide preparation while maintaining high gas permeability. High permeability is believed in the art to be the result of high molecular free volume in the polymer structure, and is further believed to result from the rigid nature of the rotationally hindered polymer chains.

In addition to the gas and chemical selectivity discussed hereinabove, polyimide membranes have been used in the context of biological constituents and reaction products. In the case of a system for the detection of biological reactions, it is known that a given protein will adhere to a substrate as a monomolecular layer, and that arbitrary protein layers will not adhere to the given protein layer. Instead, a protein which reacts specifically with the given protein will bond immunologically thereto. Such reactions have been monitored electronically with the use of a field effect transistor which includes a conventional source and drain, and employs in the gate region a layer of antibody specific to a specific antigen. When this layer communicates with an electrolyte solution containing the antigen, the charge of the protein surface changes as a result of the antigen-antibody reaction, thereby causing a change in the charge concentration in a semiconductor inversion layer in the field effect transistor. The monitoring is dynamic in that the time rate of change of drain current provides the measure of antigenic protein concentration. In some known immunological integrated circuit sensors, the layer of protein, such as the antibodies specific to an antigenic protein to be detected, is adsorbed on a thin insulating layer by immersing the device in a solution of such protein. However, other electrochemical devices which are useful in the clinical analysis of biological fluids employ ion-selective membrane layers.

In one known system, the ion-selective membrane layer is formed of an ionophoric material which is dispersed in a matrix of dielectric organic polymer. Generally, the matrix polymer is combined with a plasticizer to effect a certain amount of swelling of the polymer. This is oftentimes necessary to permit sufficient mobility of ion carriers through the membrane. Some of the plasticizers which have been used in such applications are dioctyl adipate, tris(2-ethylhexyl)phosphate, dibutyl sebacate, O-nitrophenyloctyl ether, diphenyl ether, dinonyl phthalate, dipentyl phthalate, di-2-nitrophenyl ether, glycerol triacetate, tributyl phosphate, and dioctyl phenyl phosphate. The ion-selective membranes are usually made by forming a solution of polymer, and optionally a plasticizer, in a volatile organic solvent, casting the solution onto the desired surface into the desired shape, and then removing the solvent by evaporation.

It is a problem with ion, chemical, or biological membranes that they generally are not compatible with integrated circuit manufacturing systems, and when they have been used in such environments, they have exhibited poor adherence to the silicon-based substrate. One prior art method for producing a substance-sensitive device which can be fabricated using conventional mass production technology employs a substance-sensitive photoresist layer which is compatible with large scale integrated circuit technology. In this known system, small quantities of substance-sensitive materials are dissolved and then fixed in the photoresist material by the exposure or non-exposure, to particular radiations, depending upon the type of photoresist. Thus, if a photoresist material is doped with a substance-sensitive material, and subsequently activated, a substance-sensitive layer will remain on the surface of the structure to which the photo-resist material is initially applied.

The solid state chemical sensor systems which have been produced in the prior art all suffer from one or more significant disadvantages. Those sensors which have been developed as replacements for traditional ion-sensitive electrodes, and which have used the same basic membrane technology as the ion-sensitive electrodes, have suffered from poor adhesion of the organic membrane to the chip surface. As indicated, the result has been the eventual formation of electrolyte shunts around the membrane, ultimately rendering the sensor inoperative. Those sensors which have utilized technology which is outside of the tradition for ion-selective electrodes, have suffered from unpredictable and/or unacceptable electrochemical properties. In addition, many of the sensor membranes, particularly those formed of polyvinyl chloride, are not well-suited to mass fabrication of sensors using integrated circuit techniques. Usually, membranes formed of polyvinyl chloride are applied manually.

The prior art has recognized that those polymer membranes which exhibit the preferred electrochemical properties are typically also those which are most incompatible with large scale integrated circuit fabrication. In particular, such membranes do not adhere well to the silicon-based substrate, and are not readily adapted to mask based or photolithographic dimensioning techniques. Moreover, such systems are not generally applicable to a multiplicity of solid state sensors simultaneously, such as at the wafer stage of production.

The problem of poor adherence has been recognized by the prior art and an effort at correcting the difficulty has been proposed. More specifically, it has been proposed in the art that the integrated circuit sensor be provided with a suspended mesh of polyimide. The polyimide is known to adhere well to the silicon-based substrate, and a polymeric membrane is formed in the void between the polyimide and the substrate by insertion while the polymeric membrane is in liquid form. Other systems have been proposed which utilize polyimide as a structural element for holding and/or supporting an ion-selective membrane in communication with the integrated circuit. All of these approaches to the basic problem of incompatibility of the membranes to solid state fabrication techniques require complex post IC manufacturing steps, often requiring manual operations, and yield results which are not reproducible from sensor to sensor.

It is, therefore, an object of this invention to provide a substance-sensitive solid state sensor which has an extended lifetime.

It is another object of this invention to provide a substance-sensitive membrane system for a solid state sensor which is possessed of excellent electrochemical properties.

It is also an object of this invention to provide a substance-sensitive membrane system for a solid state sensor which is characterized with excellent adherence to solid state sensor materials.

It is a further object of this invention to provide a substance-sensitive membrane system for a solid state sensor which can be applied to a plurality of solid state devices simultaneously using conventional integrated circuit manufacturing techniques.

It is additionally an object of this invention to provide a solid state sensor system which is not subject to the generation of disabling electrolyte shunts around the substance-sensitive membrane.

It is yet a further object of this invention to provide a solid state sensor system which is simple and low in cost.

It is also another object of this invention to provide a substance-sensitive polymeric membrane system for a solid state sensor which can be applied to a multiplicity of solid state devices simultaneously using conventional integrated circuit manufacturing techniques and which utilizes ionophoric doping to create the substance sensitivity.

It is yet an additional object of this invention to provide a substance-sensitive membrane for use with a solid state sensor and which does not require a structural layer associated therewith to maintain communication between the membrane and a solid state substrate.

It is still another object of this invention to provide a substance-sensitive solid state sensor which can be manufactured inexpensively in production quantities, and which can be adapted for industrial uses, such as monitoring treated or waste water for hardness or pollutants, on-line analysis of industrial chemicals, foodstuffs, and medicines, and low cost analytical instruments.

It is a yet further object of this invention to provide a substance-sensitive solid state sensor which can be manufactured inexpensively in production quantities, and which can be adapted for medical uses, such as monitoring of electrolytes, blood gases, and medical substrates.

It is also a further object of this invention to provide a substance-sensitive solid state sensor which can be manufactured inexpensively in production quantities, and which can be adapted for biochemical control systems.

It is additionally another object of this invention to provide a substance-sensitive solid state sensor which can be manufactured inexpensively in production quantities, and which can be adapted for patient monitoring and diagnostics.

A still further object of this invention is to provide a substance-sensitive membrane for use in a solid state sensor, wherein the membrane exhibits good adhesion to $SiO_2$ surfaces.

An additional object of this invention is to provide a substance-sensitive membrane for use in a solid state sensor, wherein the membrane exhibits good adhesion to $Si_3N_4$ surfaces.

SUMMARY OF THE INVENTION

The foregoing and other objects are achieved by this invention which provides an integrated circuit chemical sensor arrangement having an input electrode formed of a conductive material in the vicinity of a region formed of a silicon-based semiconductor material, the integrated circuit chemical sensor arrangement being provided with a permselective membrane having a predetermined electrochemical property. The permselective membrane is formed of a polyimide-based compound arranged to be in adherence with the silicon-based semiconductor material and in electrical communication with the input electrode, whereby the permselective membrane produces at the input electrode a voltage responsive to the electrochemical property.

In a specific illustrative embodiment of the invention, the permselective membrane is formed of a polyimide powder which is dissolved in a solvent. The solvent may be N,N-dimethylformamide (DMF). A plasticizer, which may be diethylene glycol dibenzoate, is mixed with the dissolved polyimide powder. In some embodiments, a further plasticizer may be employed, such as dipentyl phthalate.

In addition to one or more plasticizers, as described hereinabove, a lipophilic additive is combined with the mixture. Such an additive may be potassium tetrakis(p-chlorophenyl)borate.

The electrochemical property of the integrated circuit chemical sensor arrangement on the present invention is responsive, in a specific embodiment thereof, to an ionophore. The ionphore is the chemical which is added to the membrane to give it the desired electrochemical property. In a specific ion-sensitive system, the ionophore may be a calcium ionophore, such as ETH 129 and ETH 1001. Alternatively, the chemical sensor arrangement may have an electrochemical characteristic which is responsive to a different ionophore, such as an ammonium ionophore (nonactin).

Other embodiments of the invention may have electrochemical properties which are responsive to biological agents or reaction products of biological processes. In some of these embodiments, the electrochemical properties may be responsive to an enzyme, an immunochemical, a bacteria, a virus, an antibody, an antigen, etc. Thus, the integrated circuit chemical sensor arrangement of the present invention is suitable for use in the detection of substances of clinical interest.

In an alternative embodiment of the invention, the permselective membrane is comprised of a preimidized material, such as an encapsulant denominated as PI-2590-D, which is commercially available from DuPont. In such an embodiment, one or more plasticizers, such as diethylene glycol dibenzoate (DGD) and/or dipentyl phthalate (DPP) mentioned hereinabove, are mixed with the encapsulant. Also, as previously discussed, a lipophilic additive, such as potassium tetrakis(p-chlorophenyl)borate, is added to the mixture. Of course, an ionophore, or a bioactive agent, is additionally added to provide the desired electrochemical property. An ionophore is always required. However, the bioactive layer is optional.

In accordance with a process aspect of the present invention, a substance-sensitive membrane for a solid state sensor arrangement is produced by the steps of dissolving a polyimide in a solution, mixing an ionophore into the dissolved polyimide, mixing a plasticizer into the dissolved polyimide, and mixing a lipophilic additive into the dissolved polyimide.

In the practice of a specific illustrative embodiment of this process aspect of the present invention, a polyimide powder is dissolved in a solvent, such as N,N-dimethylformamide (DMF). In a further embodiment, the polyimide which is dissolved is the polyimide encapsulant known as PI-2590-D, wherein the solvent therein is N-methyl-2-pyrridone. As discussed, DMP and/or DGG are added as plasticizers, and a lipophilic additive, such as potassium tetrakis(p-chlorophenyl)borate is also added.

A film is produced by depositing the desired polyimide with the ionophore, the plasticizer(s), and the lipophilic additive mixed therein onto a substrate. The substrate may be, for example, the integrated circuit which forms the remainder of the solid state sensor, or a glass substrate from which the film membrane will be removed. After the deposition, the solvent is removed from the deposited polyimide, illustratively by subjecting same to a vacuum. As discussed, prior to deposition, an active agent is added to the mixture, which agent is an ionophore, such as a calcium ionophore, or an ammonium ionophore, an optional biologically active agent or other substance-sensitive agent, may be added as discussed herein.

In accordance with a further aspect of the invention, a substance-sensing membrane for a solid state sensor is formed of a mixture of polyimide dissolved in a solvent, an ionophore for determining the substance-sensitive electrochemical property of the substance-sensitive membrane, a plasticizer selected from the group of dimethyl phthalate and diethylene glycol dibenzoate, and potassium tetrakis(p-chlorophenyl)borate as a lipophilic additive.

BRIEF DESCRIPTION OF THE DRAWING

Comprehension of the invention is facilitated by reading the following detailed description, in conjunction with the annexed drawing, in which.

DETAILED DESCRIPTION

Polyimide-based membranes selective to ammonium, employing nonactin ionophore and calcium, employing ETH 129 and ETH 1001 ionophores, have been constructed in accordance with the present invention. It has been learned that optimization of the membrane composition requires particular attention to plasticizers, curing schedules, and to appropriate use of lipophilic additives. A first polyimide membrane composition constructed in accordance with the principles of the invention is as follows:

| POLYIMIDE MEMBRANE COMPOSITION 1 | | |
| --- | --- | --- |
| PI | 32.8 wt % | polyimide dissolved in poly(amic) acid |
| DGD | 65.6 wt % | plasticizer - diethylene glycol dibenzoate |
| KTpClPB | 0.6 wt % | lipophilic additive - potassium tetrakis(p-chlorophenyl) |

| POLYIMIDE MEMBRANE COMPOSITION 1 | | |
| --- | --- | --- |
| ETH 129 | 1.0 wt % | calcium ionophore |

Figure 1:
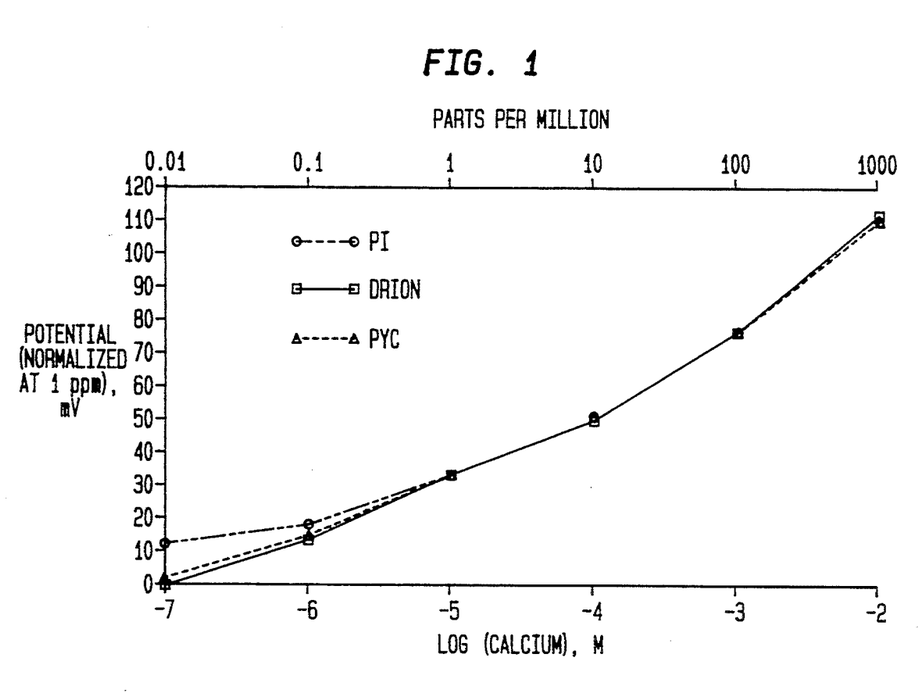
FIG. 1 is a graphical representation of the response of a calcium-selective membrane, as measured on an ion-selective electrode body.

The polyimide-based membrane of composition 1 was installed in an ion-selective electrode body, of a type which is commercially available from Phillips. FIG. 1 is a graphical representation of the response of this calcium-selective membrane, as measured on an ion-selective electrode body. This figure shows the polyimide membrane response compared to a commercial liquid-junction electrode and to a commercial PVC-based ISE.

| POLYIMIDE MEMBRANE COMPOSITION 2 | | |
| --- | --- | --- |
| PI-2590 | 600 mg | preimidized polyimide encapsulant (DuPont) |
| DGD | 50 µl | plasticizer - diethylene glycol dibenzoate |
| DPP | 50 µl | plasticizer - dipentyl phthalate |
| KTpClPB | 0.67 mg | lipophilic additive - potassium tetrakis(p-chlorophenyl). |
| Nonactin | 2 mg | ammonium ionophore |

Figure 2:
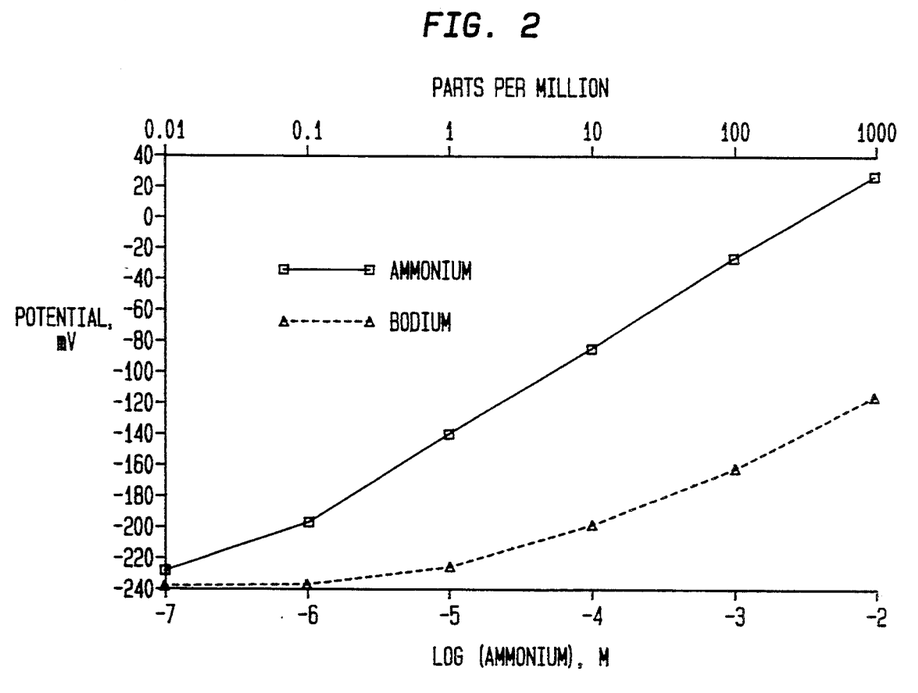
FIG. 2 is a graphical representation of a calibration curve for an ammonium-selective polyimide membrane, which illustrates the selectivity of ammonium over sodium.

FIG. 2 is a graphical representation of a calibration curve for polyimide membrane composition 2. This figure illustrates the response of the membrane of composition 2 to sodium, and demonstrates that the selectivity of the membrane for ammonium over sodium is comparable to that of PVC-based membranes.

The polyimide membranes of compositions 1 and 2 were formed by solvent casting on glass. The membranes were then installed on a ion-selective electrode body for electrochemical characterization. The polyimide membranes exhibited outstanding properties of adhesion to glasses. Moreover, these films exhibit excellent stability, and have been shown through experimentation to retain 90% of their initial tensile strength after 1000 hours at 300° C. The membranes are resistant to most organic solvents, and are degraded somewhat by aqueous acids and alkalis.

It is contemplated within the scope of the present invention that numerous techniques for applying the membranes to integrated circuit systems can be employed. These techniques include, for example, dipping, casting, spin coating, and screen printing. Moreover, numerous variations in the specific composition can be made, and result in useful membranes. At the present time, the simplest membranes are those which contain ionophore to a specific ion. Such membranes could also be used in conjunction with, or incorporate in the membrane matrix, a bioactive agent, such as an enzyme, an immunochemical, a bacteria, etc. The introduction of such agents into the membrane will result in specificity for complex chemicals.

EXPERIMENTS

Apparatus

The measurements of the potentiometric characteristics of the membranes was performed by mounting the membranes in Phillips electrode bodies (IS-561)(Glasblaserei Möller, Zurich). The external reference was an Orion sleeve-type double junction Hg/AgCl electrode (Model 90-02). The electrodes were connected through a high impedance amplifier to a Zenith Z-100 personal computer equipped with an analog-to-digital converter (DT 2801, Data Transaction Inc., Marlborough, Mass.).

Reagents

The reagents used in the experiments discussed herein were as follows:

poly(vinyl chloride) high molecular weight (PVC); dibutyl sebacate (DBS); o-nitrophenyl octyl ether (o-NPOE); nonactin; calcium ionophore II (ETH 129); and potassium tetrakis(p-chlorophenyl)borate (KTpClPB) were obtained from Fluka (Ronkonkoma, N.Y.); polyimide (PI—fully imidized and polymerized); plasticizer sample kit 301 (90 different plasticizers, including dimethyl phthalate (DMP) and diethyl glycol dibenzoate (DGD)) were purchased from Scientific Polymer Products, Inc. (Ontario, N.Y.); anhydrous tetrahydrofuran (THF—water content <0.005% ) and N,N-dimethylformamide (DMF—water content <0.005%) obtained from Aldrich Chemical Company, Milwaukee, Wis.; dipentyl phthalate (DPP) from Eastman Kodak, Rochester, N.Y.; pyralin LTP (PI-2590-D-preimidized polyimide encapsulant from Dupont Company, Wilmington, Dela.). All other chemicals used were analytical-reagent grade. Standard solutions and buffers were prepared with deionized water.

Preparation of Ion-Selective Membranes

Polyimide-based ion-selective membranes were formed by dissolving polyimide (PI) powder in DMF (25% w/w) by heating the solution to 120° C. Various membranes having different compositions were then prepared by mixing the PI solution with membrane active components, including ionophore, plasticizer, and lipophilic additives. The mixture was applied dropwise to a glass plate, and the solvent (DMF) was allowed to evaporate for two days under vacuum. The membranes which employed the PI-2590-D polyimide encapsulant were formed by mixing the encapsulant directly with the membrane active components and applying same to the glass plate. In this case, however, longer evaporation periods, on the order of 4-5 days, were employed as a result of the high boiling point of the solvent (N-methyl-2-pyrrolidone) which is used in PI-2590-D.

PVC-based ion-selective membranes were formed by incorporating nonactin and ETH 129, respectively, into PVC membranes. The preparation of such membranes is known to persons skilled in the art.

Evaluating Potentiometric Response

Small disks were punched from the membranes formed on the glass plates, and mounted in Phillips electrode bodies. In the case of the polyimide membranes, a sharp razor blade was used to detach the membranes from the glass. The inner filling solution varied, depending upon which ion-selective membrane was being evaluated. For example, 0.1 M $NH_4Cl$ was used for $NH_4^+$-selective membranes, and 0.01 M $CaCl(2)$ was used for $Ca^{2+}$-selective membranes. The calibration plots were obtained from additions of standard solutions to 250 ml of background electrolyte (0.05M Tris-HCl having pH 7.2) at room temperature. The selectivity coefficients were determined by the known separate solution method.

Evaluating Adhesion Characteristics

Adhesion characteristics were evaluated using a known method. For each membrane type, ten membranes were cast by drops onto a silicon wafer coated with 10,000 Å of plasma-deposited silicon nitride. In the case of the polyimide membranes, an adhesion promoter (VM-651, DuPont Company, Wilmington, Dela.) was applied to the wafer before casting the membranes. After the membranes were cured, the wafers were immersed in an ultrasonic bath (Branson Cleaning Equipment, Smithkline Company, Shelton, Conn.), the time to detachment was recorded for each membrane.

Results

The inventors herein have discovered that the plasticizers which are frequently used in the preparation of PVC-based ion-selective membranes, such as DBS, DOA, o-NPOE, etc., were not compatible with polyimide. In fact, among more than 90 plasticizers tested for incorporation in polyimide matrices, only two, dimethyl phthalate (DMP) and diethylene glycol dibenzoate (DGD), resulted in transparent, flexible, yet mechanically strong membranes. Incorporation of these plasticizers into the polyimide matrix appeared to have little effect on the excellent adhesion properties of the resulting membranes toward glass surfaces. As indicated, these membranes can not be pulled free from the glass, but must be cut from the glass plate with a razor blade.

In order to examine the feasibility of using polyimide as the matrix of ion-selective membranes, nonactin (2 mg) was incorporated into polyimide-matrix membranes (75 mg of PI) along with a plasticizer, DMP or DGD (130 μl).

Figure 3:
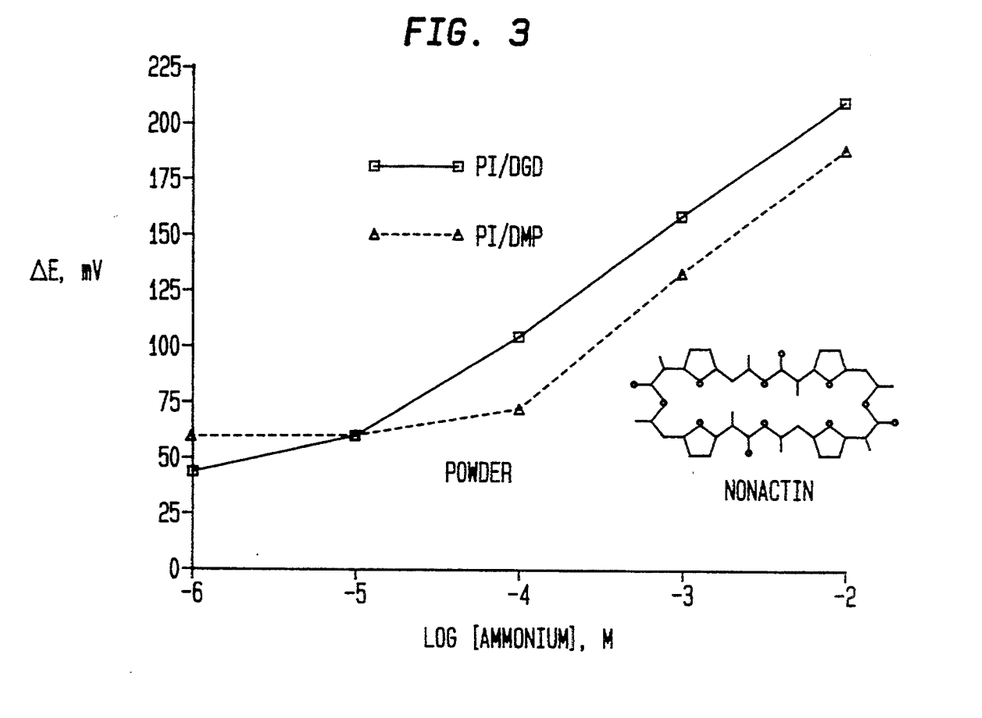
FIG. 3 is a graphical representation of the potentiometric response of a polyimide membrane constructed in accordance with the invention, toward ammonium ions.

FIG. 3 is a graphical representation of the potentiometric response of a polyimide membrane constructed in accordance with the invention toward ammonium ions. As can be seen, the polyimide membrane prepared with DGD exhibited better response characteristics, i.e, lower detection limits, than that prepared with DMP. However, the response characteristic of the DGD-based polyimide membranes exhibited a slope 50 mV per decade or $10^{-5}$ to $10^{-2}$ moles $NH_4^+$. This characteristic is inferior to those membranes which are PVC-based.

Figure 4:
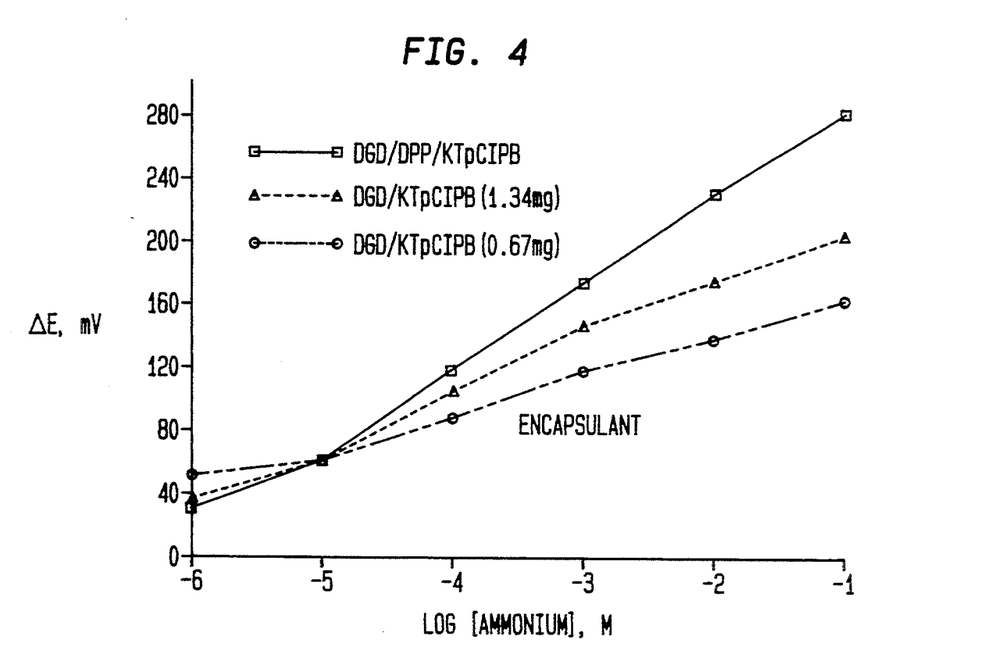
FIG. 4 is a graphical representation of the potentiometric response of a polyimide membrane toward ammonium ions, the membrane having an increased amount of lipophilic additive and mixed plasticizer.

In an effort to improve the performance of the polyimide matrix membrane, several membranes were prepared which incorporated additional lipophilic additives, or other plasticizers, in addition to nonactin or polyimide. PI-2590-D encapsulant was used in these membranes. An increase in the amount of lipophilic additive (KTpClPB) in the membrane phase increased the response slope of the resulting PI-2590-D matrix membrane. This improvement in the response is evident in the graphic representation of FIG. 4. This figure is a graphical representation of the potentiometric response of a polyimide membrane toward ammonium ions, the membrane having an increased amount of lipophilic additive. The potentiometric response was further improved when the membrane was prepared by using an additional plasticizer, dipentyl phthalate (DPP), which previously had been used for the preparation of the $NH_4^+$-selective polymer membranes.

Although the incorporation of DPP into the PI-2590-D matrix produced a less transparent membrane, the resulting membrane retained its high mechanical strength and homogeneity. As is evident from FIG. 4, the response of the membrane was greatly enhanced by using the mixed plasticizer (DGD/DPP; 50 μl/50 μl) and KTpClPB (0.67 mg), along with nonactin (2 mg) and PI-2590-D (600 mg).

Figure 5:
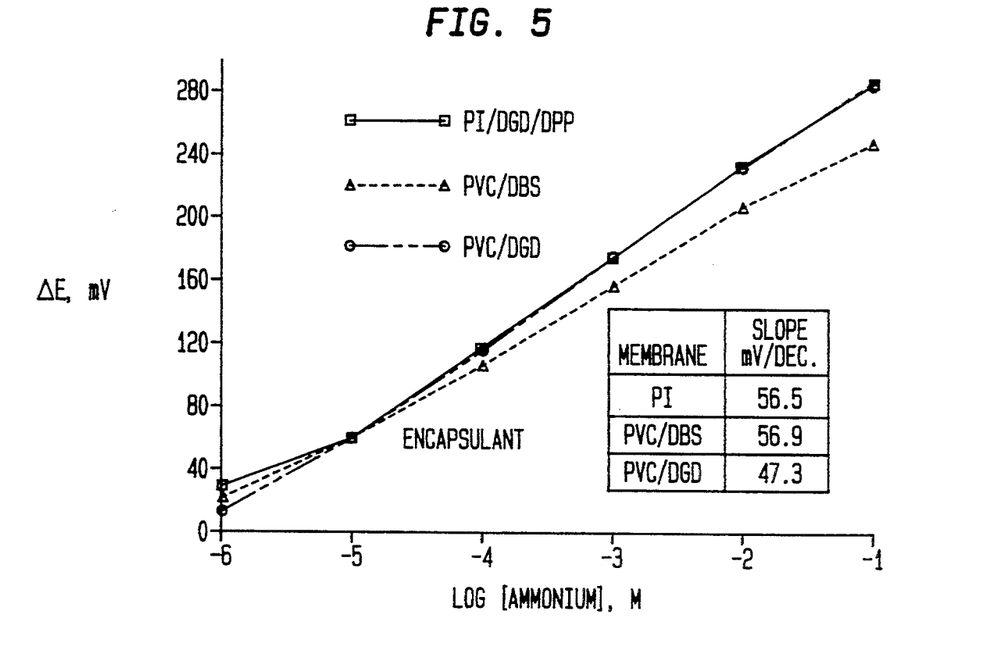
FIG. 5 is a graphical representation of the potentiometric response of PVC-based membranes formed using DGD as the plasticizer.

The potentiometric response of the optimized $NH_4^+$-selective PI-2590-D matrix membrane was compared to those of PVC-based membranes. FIG. 5 illustrates that PVC-based membranes prepared using DGD as the plasticizer had significantly degraded response toward $NH_4^+$. As shown in FIG. 5, this membrane exhibits a slope of 47.3 mV per decade over the range of $10^{-5}$ to $10^{-1}$ M $NH_4^+$. However, the optimized PI-2590-D membranes exhibited nearly the same response slope (56.5 mV per decade) as those found for the conventional PVC-based membrane (56.9 mV per decade). In addition, the selectivity coefficients, which correspond to:

$$\log k^{pot}_{NH_4+}$$

obtained for the PI-2590-D matrix membrane (−0.9 for K+; −2.7 for Na+) were similar to those for PVC-based membranes (−0.9 for K+; −2.9 for Na+).

The polyimide matrix was further evaluated by preparing $Ca^{2+}$-selective membranes. For this, ETH 129 (2 mg) was incorporated with KTpClPB (1.2 mg), DGD (66 μl), and polyimide (PI 66 mg).

Figure 6:
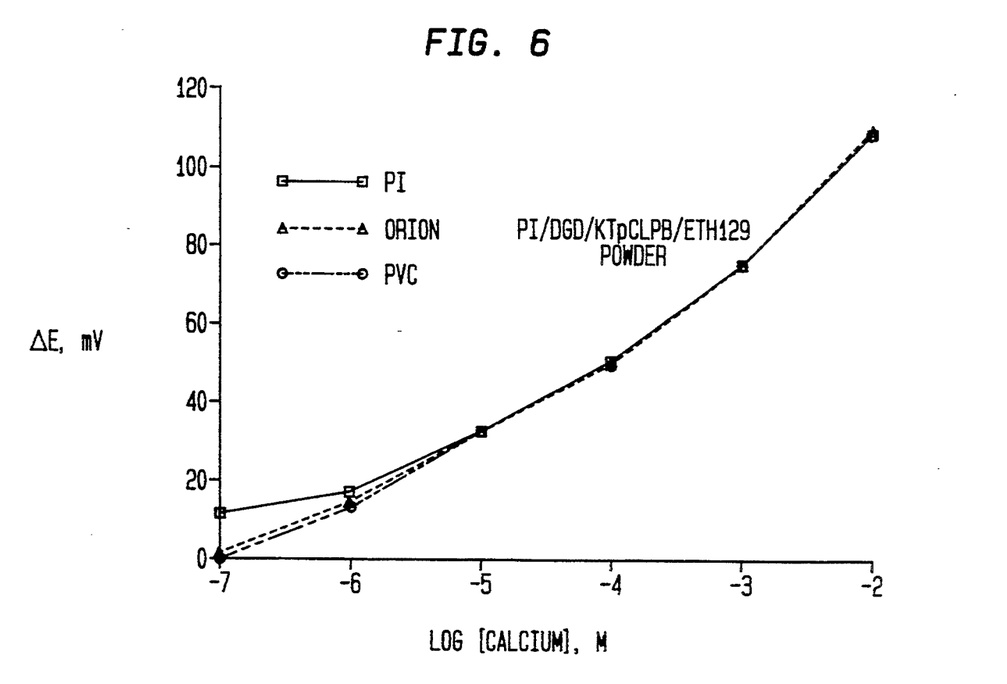
FIG. 6 is a graphical representation of a comparison of the potentiometric response of the polyimide membrane to those of conventional PVC and liquid-type $Ca^{2+}$-selective electrodes.

FIG. 6 is a graphical representation of the potentiometric response of the polyimide matrix membrane, compared to those of conventional PVC and commercial Orion liquid-type $Ca^{2+}$-selective electrodes. The performance of these electrodes is seen to be comparable except for a slightly higher detection limit for the polyimide matrix membrane.

Figure 7:
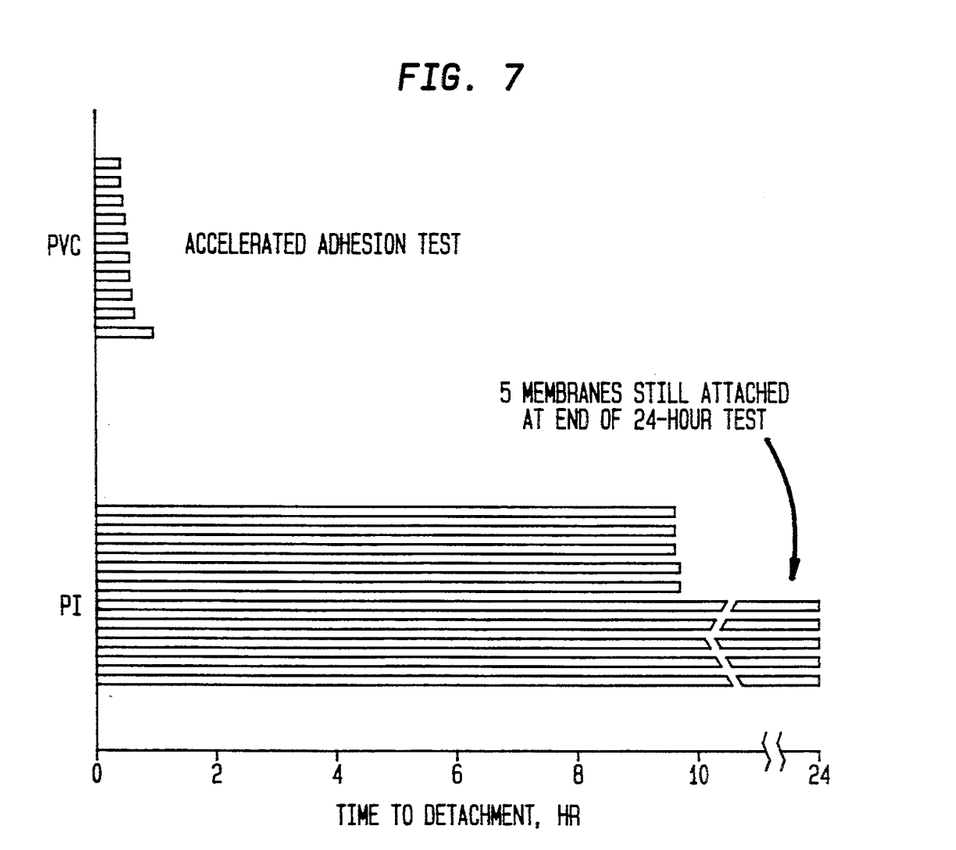
FIG. 7 is a graphical illustration of the adhesion characteristics of the polyimide membranes as compared to PVC membranes.

As expected, the polyimide membranes exhibited much better adhesion to the silicon nitride surface than did PVC membranes. FIG. 7 is a graphical illustration of the adhesion characteristics of the polyimide membranes, as compared to PVC membranes. As shown, detachment of the ten PVC membranes occurred over a range of 25 to 60 minutes, with the median time being 31 minutes. Five polyimide membranes detached almost in unison between 9 hours and 37 minutes and 9 hours and 40 minutes. The remaining five remained intact when the test was terminated after 24 hours. The median polyimide membrane lifetimes in this test were, therefore, more than 25 times longer than that of the PVC membranes.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An integrated circuit chemical sensor arrangement comprising:
   an input electrode formed of a conductive material in the vicinity of a region formed of a silicon-based semiconductor material; and
   a permselective membrane having an ion-selective electrochemical property and formed by dissolving a polyimide-based compound in a solvent with a plasticizer selected from the group consisting of dimethy phthalate (DMP) and diethylene glycol dibenzoate LDGD), and a neutral carrier ionophore and then removing said solvent, whereby said plasticizer and said neutral carder ionophore are uniformly distributed in said polyimide-based compound, said permselective membrane being arranged to be in adherence with said silicon-based semiconductor material and in electrical communication with said input electrode, for producing at said input electrode a voltage responsive to said electrochemical property, whereby said permselective membrane is formed of solidified polyimide.

2. The integrated circuit chemical sensor arrangement of claim 1 wherein said polyimide-based compound in said permselective membrane is made from a polyimide powder.

3. The integrated circuit chemical sensor arrangement of claim 2 wherein said solvent is N,N-dimethylformamide (DMF).

4. The integrated circuit chemical sensor arrangement of claim 2 wherein said permselective membrane is further comprised of a lipophilic additive.

5. The integrated circuit chemical sensor arrangement of claim 4 wherein said lipophilic additive is potassium tetrakis (p-chlorophenyl) borate.

6. The integrated circuit chemical sensor arrangement of claim 1 wherein said neutral carrier ionophore renders the integrated circuit chemical sensor arrangement responsive to calcium.

7. The integrated circuit chemical sensor arrangement of claim 1 wherein said sensor is responsive to a bioactive agent.

8. The integrated circuit chemical sensor arrangement of claim 7 wherein said bioactive agent is selected from the group consisting of an enzyme, an immunochemical, a bacteria, and a virus.

9. The integrated circuit chemical sensor arrangement of claim 1 wherein said permselective membrane is comprised of a material which has been subjected to imidization.

10. The integrated circuit chemical sensor arrangement of claim 9 wherein said preimidized material is pyralin LTP.

11. The integrated circuit chemical sensor arrangement of claim 9 wherein said permselective membrane is further comprised of a lipophilic additive.

12. The integrated circuit chemical sensor arrangement of claim 11 wherein said lipophilic additive is potassium tetrakis (p-chlorophenyl) borate.

13. The integrated circuit chemical sensor arrangement of claim 1 wherein said plasticizer is dipentyl phthalate.

* * * * *